United States Patent
Longo et al.

(10) Patent No.: US 9,974,857 B2
(45) Date of Patent: May 22, 2018

(54) CONJUGATE OF A FRAGMENT OF A CELLULAR WALL OF A BACTERIUM AND A MUCOPOLYSACCHARIDIC CARRIER, AND USES IN MEDICINE THEREOF

(71) Applicant: Claride Pharma S.A., Lugano (CH)

(72) Inventors: Sonia Longo, Sesto S. Giovanni (IT); Bernard Bizzini, Carcassonne (FR); Ivo Volpato, Corciano (IT)

(73) Assignee: Claride Pharma, S.A., Lugano (CH)

( * ) Notice: Subject to any disclaimer, the term of this patent is extended or adjusted under 35 U.S.C. 154(b) by 0 days. days.

(21) Appl. No.: 15/446,824

(22) Filed: Mar. 1, 2017

(65) Prior Publication Data

US 2017/0173163 A1    Jun. 22, 2017

Related U.S. Application Data

(62) Division of application No. 14/430,671, filed as application No. PCT/IB2013/058842 on Sep. 25, 2013, now abandoned.

(30) Foreign Application Priority Data

Sep. 25, 2012 (IT) .............................. MI2012A1597

(51) Int. Cl.
| | |
|---|---|
| *A61K 31/22* | (2006.01) |
| *A61K 45/06* | (2006.01) |
| *A61K 39/05* | (2006.01) |
| *A61K 9/00* | (2006.01) |
| *C08B 37/08* | (2006.01) |
| *C08B 37/00* | (2006.01) |
| *A61K 47/61* | (2017.01) |

(52) U.S. Cl.
CPC ............ *A61K 45/06* (2013.01); *A61K 9/0014* (2013.01); *A61K 9/0034* (2013.01); *A61K 39/05* (2013.01); *A61K 47/61* (2017.08); *C08B 37/0069* (2013.01); *C08B 37/0072* (2013.01); *C08B 37/0075* (2013.01)

(58) Field of Classification Search
CPC ...... C07H 13/04; A61K 31/22; A61K 31/222; A61K 31/223; A61K 31/225; A61K 31/23; A61K 31/575; A61K 31/661; A61K 31/683; A61K 31/685; A61K 31/695; A61K 31/70; A61K 31/7004; A61K 31/7012; A61K 31/7016; A61K 31/702
See application file for complete search history.

(56) References Cited

U.S. PATENT DOCUMENTS 4,479,935 A * 10/1984 Metianu ................ A61K 35/74
424/245.1

2002/0049183 A1 * 4/2002 Yedgar ............ A61K 47/48053
514/54
2003/0099672 A1    5/2003 Schultz

FOREIGN PATENT DOCUMENTS

| EP | 0433744 | * 12/1990 | ............ A61K 35/74 |
|---|---|---|---|
| EP | 0433744 A1 | 6/1991 | |
| EP | 0497525 A2 | 8/1992 | |
| EP | 1234584 A1 | 8/2002 | |
| EP | 1243256 A1 | 9/2002 | |
| EP | 2201961 A1 | 6/2010 | |
| WO | 0168128 A1 | 9/2001 | |
| WO | 2009143413 A1 | 11/2009 | |
| WO | 2009149155 A1 | 12/2009 | |
| WO | 2010145821 A1 | 12/2010 | |
| WO | WO 2010145821 | * 12/2010 | ............ C08B 37/00 |

OTHER PUBLICATIONS

Bizzini et al., "Induction of Various Cytokines in Mice and Activation of the Complement System in Rats as a Part of the Mechanism of Action of the Corynebacterium Granulosum-Derived P40 Immunomodulator," FEMS Microbial. Immunol. 5(4):171-180 (1992) (abstract).
Henocq et al., "Treatment of Recurrent Urogenital Infections by Immunomodulation," Ann. Urol. (Paris) 19(6):371-375 (1985) (abstract).
Schubert & Hamerman, "A Primer on Connective Tissue Biochemistry," Book Reviews, Ann. Rheum. Dis. 28:191 (1969) (abstract).
Toole, "Glycosaminoglycans in Morphogenesis," in Hay, ed., Cell Biology of Extracellular Matrix, New York, NY: Plenum Press, pp. 259-294 (1981).
Scher & Hamerman, "Isolation of Human Synovial-Fluid Hyaluronate by Density-Gradient Ultracentrifugation and Elevation of Its Protein Content," Biochem. J. 126(5):1073-1080 (1972).
Smith & Gallop, "The 'Acid Polysaccharides' of Hog Gastric Mucosa," Biochem. J. 53(4):666-672 (1953).
Kraemer, "Heparan Sulfates of Cultured Cells. I. Membrane-Associated and Cell-Sap Species in Chinese Hamster Cells," Biochem. 10(8):1437-1445 (1971).
Meyer et al., "The Acid Mucopolysaccharides of Connective Tissue," Biochim. Biophys. Acta 21:506-518 (1956).
Mathieu et al., "*E. coli* Infections of the Lower Urinary Tract and Their Treatment by Immunomodulation or Combined Immunomodulation and Antigen Therapy," Biomed. Pharmacother. 42(4):271-277 (1988) (abstract).
Fattal-German & Bizzini, "The Corynebacterium Granulosum-Derived P40 Immunomodulator Exerts a Synergistic Effect on the Activity of Antiviral Drugs in the Treatment of Experimental Viral Infections," Biomed. Pharmacother. 42 (3):217-220 (1988) (abstract).

(Continued)

*Primary Examiner* — Jana A Hines
(74) *Attorney, Agent, or Firm* — LeClairRyan PLLC

(57) ABSTRACT

The present invention relates in one aspect to a conjugate of a mucopolysaccharide or mucopolysaccharidic fraction and a cellular wall fragment of a bacterium belonging to the *Corynebacterium* genus, and in particular to the *Corynebacterium granulosum* species, also named P40. The conjugate of the invention is applied to medicine, in particular for topical treatment of infections, dermatological affections, such as psoriasis, acne, allergic reactions, such as rashes and eczema, and in vaginal mucosae affections.

14 Claims, No Drawings

(56) References Cited

OTHER PUBLICATIONS

Bizzini & Fallal-German, "Potentiation by Nonspecific Immunostimulation of the Efficacy of Antibiotics in the Treatment of Experimental Bacterial Infections," Biomed. Pharmacother. 43(10):753-761 (1989) (abstract).
Henocq et al., "Preliminary Experimental and Clinical Results With Inactivated Allergens Conjugated to the Corynebacterium Granulosum-Derived Immunomodulator P40," Boll. 1st. Sieroter Milan 66(1):70-77 (1987) (abstract).
Vaheri & Alitalo, "Pericellular Matrix Glycoproteins in Cell Differentiation and in Malignant Transformation," in Lloyd, eds., Cellular Controls in Differentiation, London:Academic Press, pp. 29-56 (1981).
Baker et al., "The Linkage of Corneal Keratan Sulfate to Protein," Connect. Tissue Res. 3(2):149-156 (1975) (abstract).
Bizzini & Faffal-German, "Standardized Mouse Infection Models as a Way of Evaluating the Potency of Anti-Infectious Agents," Dev. Biol. Stand. 77:137-142 (1992) (abstract).
Fattal-German & Bizzini, "Assessment of the Anti-Viral Effect of a Short-Term Oral Treatment of Mice With Live *Saccharomyces cerevisiae* Cells," Dev. Biol. Stand. 77:115-120 (1992) (abstract).
Mastroeni et al., "The Restoration of Impaired Macrophage Functions Using as Immunomodulator the Corynebacterium Granulosum-Derived P40 Fraction," Immunopharmacology 10(1):27-34 (1985) (abstract).
Bizzini & Faffal-German, "Use of Live *Saccharomyces cerevisiae* Cells as a Biological Response Modifier in Experimental Infections," FEMS Microbiol. Immunol. pp. 155-168 (1990).
Reynier et al., "Immunological Investigation and Immunotherapy in Patients Operated on for Breast Carcinoma," Int. Surg. 67(1):17-24 (1982) (abstract).
Reynier et al., "An Experimental and Clinical Study of Immunocompetence and Immunostimulation in Breast Cancer," Int. Surg. 73(1):10-15 (1988) (abstract).
Kleinman et al., "Role of Collagenous Matrices in the Adhesion and Growth of Cells," J. Cell Biol. 88:473-485 (1981).
Meyer et al., "Hyaluronidases of Bacterial and Animal Origin," J. Exp. Med. 73(3):309-326 (1941).
Hobby et al., "The Relationship Between Spreading Factor and Hyaluronidase," J. Exp. Med. 73(1):109-123 (1941).
Danishefsky & Bella, "The Sulfated Mucopolysaccharides From Human Umbilical Cord," J. Biol. Chem. 241(1):143-146 (1966).
Lamberg et al., "Glycosaminoglycans. A Biochemical and Clinical Review," J. Invest. Dermatol. 63:433-449 (1974).
Sluke et al., "Age-Related Changes in the Distribution Pattern of Glycosaminoglycans Synthesized by Cultured Human Diploid Fibroblasts (WI-38)," Mech. Ageing Dev. 16(1):19-27 (1981) (abstract).
Jacques et al., "Variations in the Phagocytic Potency of Circulating Leukocytes From Rats Which Received a Thermal Injury. Effects of an Immunostimulation With Corynebacterium Granulosum," Pathol. Biol (Paris) 26(8):495-502 (1978) (abstract).
Kanwar & Farquhar, "Presence of Heparan Sulfate in the Glomerular Basement Membrane," Proc. Nat'l. Acad. Sci. U.S.A. 76(3):1303-1307 (1979).
Relyveld et al, "Synergy Between Low-Dose Chemotherapy and Immunotherapy in Mouse L1210 Leukemia," Cancer Treat. Rep. 71(3):241-246 (1987) (abstract).
Grobstein, "Developmental Role of Intercellular Matrix: Retrospective and Prospective," in Slavkin, eds., Extracellular Matrix Influences on Gene Expression, New York, NY:Academic Press, pp. 9-16 (1975).
Bizzini et al., "Isolement et Caractérisation d'une fraction, dite fraction P40 à Partir de Corynebacterium Granulosum," Medecine et Maladies Infectieuses 9(8):408-414 (1978) (English abstract).
Marbet & Winterstein, "Probleme der Blutgerinnung. 4. Mitteilung. Beta-Heparin, ein Neuer, Blutgerinnungshemmender Mucoitinschwefelsaureester," Helv. Chim. Acta 34(7):2311-2320 (1951).
Bizzini et al., "Potentiation by Nonspecific Immunostimulation of the Efficacy of Antibiotics in the Treatment of Experimental Bacterial Infections," Biomed. & Pharmacother. 43:753-762 (1989).
Morales et al., "838 Phase 1 Study with Mycobacterial Cell Wall Extract and Hyaluronic Acid for the Intraprostatic Treatment of Localised Prostate Cancer," European Urology Supplements 3(2):212 (2004).
Bizzini et al., "Induction of Various Cytokines in Mice and Activation of the Complement System in Rats as a Part of the Mechanism of Action of the Corynebacterium Granulosum-Derived p40 Immunomodulator," FEMS Microbiology Immunology 105:171-180 (1992).
International Search Report and Written Opinion of corresponding application No. PCT/IB2013/058842, dated Mar. 27, 2014.

\* cited by examiner

CONJUGATE OF A FRAGMENT OF A CELLULAR WALL OF A BACTERIUM AND A MUCOPOLYSACCHARIDIC CARRIER, AND USES IN MEDICINE THEREOF

This application is a divisional of U.S. patent application Ser. No. 14/430,671, filed Mar. 24, 2015, which is a national stage application under 35 U.S.C. § 371 of PCT International Application No. PCT/IB2013/058842, filed Sep. 25, 2013, which claims the benefit of Italy Application No. MI2012A001597, filed on Sep. 25, 2012, which are hereby incorporated by reference in their entirety.

FIELD OF THE INVENTION

The present invention relates to a conjugate of a fragment of a cellular wall of a bacterium and a mucopolysaccharidic carrier, and uses in medicine thereof.

The present invention originates in the sector of products for medical use, in particular intended for topical application.

STATE OF THE ART

The natural defense systems of the human body protect the organism from aggressions from the external environment.

Notoriously, the first barrier to external aggressions, such as those of microbic, toxic or environmental type, is in the skin, which acts as physical barrier.

The natural (non specific) immunity agents which constitute the immune defense frontline intervene on subcutaneous-submucosal level when this barrier is crossed, such as in case of particularly virulent bacterial or viral infections or in presence of a skin lesion. These agents are mainly macrophages and some blood factors, such as the immune system components. The function of macrophages (polynucleated cells) is to ingest and kill the aggressors, usually consisting of bacteria, fungi or viruses.

Most of the time the defense frontline can eliminate the aggressing agent, but the second frontline of defense (specific adaptive immunity, of both humoral antibody-mediated and cell-mediated type, which puts cytotoxic cells into circulation) is activated when the agent is excessively virulent.

The induction of specific immunity is the result of the 'process' implemented by the macrophages on the antigens of the aggressors and the presentation of given antigens to the cells involved in the humoral- or cell-mediated responses. Epidermal macrophages are Langerhans cells, dendritic cells and keratinocytes capable of 'processing' the antigens; furthermore, these cells release cytokines, which attract lymphocytes towards the site of the aggression causing an inflammatory defense reaction to develop.

However, the macrophages will not be able to contrast the aggression and a disease condition will be established if the immune status of the organism is compromised, e.g. due to the prolonged use of antibiotic treatments, infections, active tumors, or if the pathogen agent is particularly virulent.

In normal conditions, macrophages cannot ensure their function when the invading agent is an excessively large population of microorganisms, or in the case of an intercellular-developing microorganism, such as for example a bacterium (*L. monocytogenes*), a fungus (*C. albicans*), or a virus, such as the herpetic virus, which have an additional immunosuppressive action.

Substances named 'immunomodulatory' may be administered in order to restore the functionality of debilitated macrophages or to potentiate their activities involved in a particularly severe aggression. Generally, these are inactivated microorganisms which are capable of stimulating the immune system, such as for example *M. tuberculosis* and derivates thereof, which are used as Freund's adjuvant components in the preparation of parenteral vaccines, and other products which stimulate the reticuloendothelial system and strengthen immune defense.

Immune system alteration is one of the most relevant aspects of cutaneous-mucosal pathologies, such as for example infective, inflammatory, allergic, vascular disorders, in which a plurality of mechanisms are involved.

Currently, the need is felt for immunostimulating preparations, which applied locally are capable of activating an anti-body response in response to infections of various origin, such as bacterial, viral or fungal infections.

It is one of the general objects of the present invention to provide a product for topical application which crosses the external layers of the epidermis reaching the deeper layers in which it may promote an adequate natural non-specific immunity response and/or a specific adaptive immunity response.

SUMMARY

The inventors of the present invention have identified, in accordance with an aspect of the invention, the possibility of activating and/or promoting some non-specific endogenous immune defense mechanisms by locally applying a product on the skin, in which fractions of a cellular wall of a bacterium are conjugated with specific carriers which allow to cross the skin barrier and reach the zones in which the immunocompetent cells are located.

In view of the aforementioned objects, a first aspect of the present invention relates to a conjugate of a fragment or fraction of cellular wall of a *Corynebacterium* and a physiologically acceptable carrier comprising a mucopolysaccharide or a mucopolysaccharidic fraction.

According to some embodiments, a conjugate of a fragment or fraction of cellular wall of *Corynebacterium granulosum* P40 and a physiologically acceptable mucopolysaccharide-based carrier or a physiologically acceptable mucopolysaccharidic fraction is provided.

The applicant has surprisingly observed that covalent P40-mucopolysaccharidic fraction conjugates when applied on mucosae or skin, determine a synergistic effect for the treatment of allergic skin affections, disorders (such as fat, wrinkles, skin ageing), infections, inflammations (such as eczemas, psoriasis, acne, erythemas, burns, ulcers) or vascular matrix affections (such as varicose veins, phlebitis, thrombophlebitis, peripheral vascular thrombosis).

The synergistic action is determined in part by the fact that the mucopolysaccharides in conjugated form with P40 applied onto the skin or mucosae put insoluble particle cell fragments into contact with the cutaneous/subcutaneous tissue, thus promoting the activation of subcutaneous immunocompetent cells and non-specific endogenous and immune-defense mechanisms.

In accordance with a specific aspect, the present invention relates to a conjugate of a fragment of a cellular wall of a bacterium belonging to the genus *Corynebacterium*, in particular *Corynebacterium granulosum*, and a physiologically acceptable carrier, comprising a mucopolysaccharide or a mucopolysaccharidic fraction for use as a medicament.

In accordance with a third aspect, the present invention relates to a conjugate of a fragment of a cellular wall of a bacterium belonging to the genus *Corynebacterium* and a physiologically acceptable carrier, comprising a mucopolysaccharide or a mucopolysaccharidic fraction for topical use in the treatment of bacterial, viral or fungal infections.

In accordance with a fourth aspect, the present invention relates to a conjugate of a fragment of a cellular wall of a bacterium belonging to the genus *Corynebacterium* and a physiologically acceptable carrier comprising a mucopolysaccharide or a mucopolysaccharidic fraction for topical use in the treatment of dermatological affections or pathologies.

In accordance with a fifth aspect, the present invention relates to a conjugate of a fragment of a cellular wall of a bacterium belonging to the genus *Corynebacterium* and a physiologically acceptable carrier comprising a mucopolysaccharide or a mucopolysaccharidic fraction for topical use in the treatment of allergic skin disorders or affections.

In accordance with a sixth aspect, the present invention relates to a conjugate of a fragment of a cellular wall of a bacterium belonging to the genus *Corynebacterium* and a physiologically acceptable carrier comprising a mucopolysaccharide or a mucopolysaccharidic fraction and a pharmaceutically or physiologically acceptable excipient.

In accordance with some embodiments, the composition of the invention is suited for topical application.

In accordance with a further aspect, the present invention relates to a conjugate of a fragment of a cellular wall of a bacterium belonging to the genus *Corynebacterium*, in particular *Corynebacterium granulosum* (P40) and a physiologically acceptable collagen-based carrier and to uses in medicine thereof, with particular reference to the applications described hereinafter.

DETAILED DESCRIPTION OF THE INVENTION

According to given aspects of the invention, the applicant found that by conjugating an isolated insoluble fraction of the *Corynebacterium granulosum* bacterium, named P40, with a mucopolysaccharide or a mucopolysaccharidic fraction, the P40 can be carried into the deep layers of the skin so as to stimulate the macrophage activity of the Langherans cells and of the keratinocytes, thus determining a local non-specific immunity response and a specific adaptive immunity response.

In accordance with a first aspect, the present invention provides a conjugate of a fragment of cellular wall of *Corynebacterium granulosum* and of a physiological acceptable mucopolysaccharide or mucopolysaccharidic fraction based carrier. Specifically, a P40-physiologically acceptable covalent conjugate carrier is provided, wherein the physiologically acceptable carrier comprises a physiologically acceptable mucopolysaccharide or mucopolysaccharidic fraction.

In the scope of the invention, the expression 'fragment of a cellular wall' means a portion of the cellular wall of a bacterium or a bacterial lysate. A suitable fragment of cellular wall of bacterium either consists of or comprises P40.

The term 'P40' as used herein means an insoluble fraction or fragment isolated from the bacterium *Corynebacterium granulosum*. As a non-specific immunostimulant, *Corynebacterium granulosum* P40 activates the reticuloendothelial system, induces the production of certain cytokines, enhances macrophage activity, and potentiates a delayed-type hypersensitivity response when co-administered with an antigen.

In accordance with some embodiments, the fragment of cellular wall of *Corynebacterium granulosum* named P40 is obtained according to the method described in the publication by B. Bizzini, B. Maro and P. Lallouette, Isolement et caractérisation d'une fraction, dite fraction P40 à partir de *Corynebacterium granulosum*, Med. et Mal. infect., 1978, 408-414.

In some aspects, the invention relates to a conjugate of P40 and a physiologically acceptable mucopolysaccharide or a mucopolysaccharidic fraction.

In some embodiments, the fragment of cellular wall of a bacterium P40 present in the conjugate of the invention is delipidated, i.e. treated so as either to remove or considerably reduce the lipid component of the cellular wall of the bacterium by means of chemical techniques.

For example, the bacterium, in particular *Corynebacterium granulosum*, is delipidated prior to crushing to produce the cellular wall fragments, as in the case of the P40 fraction.

Typically, the delipidated fragments of cellular wall comprise sugars and peptidic chains, typically bound to one another into glycopeptides which form a close knit mesh. Typical sugars of the cellular wall comprise N-Acetylmuramic acid and N-Acetylglucosamine.

It has been observed that the fragments or lysates of walls of *C. granulosum* stimulate the macrophage activity of Langerhans cells and of keratinocytes, which are involved in the non-specific natural immune response and, secondarily, in the specific adapted immune response.

An advantage deriving from the use of fragments (P40) of wall of *Corynebacterium granulosum* in the conjugate is determined by the absence of absorption when the conjugate is administered topically; in this manner, the risks of onset of undesired side effects or systematic toxicity are considerably limited.

The fragments of cellular wall P40 has been proven to be capable of developing a high number of pharmacological effects, such as, for example:

inhibiting L1210 tumor development in mice (E. H. Relyveld, B. Bizzini, R. Ophir and S. Ben-Efraim, Synergy between low-dose chemotherapy and immunotherapy in mouse 1210 leukemia, Cancer Treatment Report, 1987, 71, 241-246), adjuvant effects (E. Henocq, J. C. Bazin, B. Bizzini and J. Reynier, Adjuvant P40 et reactions cutanées à l'antigène. Med. Mal. infect., 1978, 8, 415-421), immunomodulatory effects (B. Bizzini, E. Henocq, J. Reynier and E. H. Relyveld, Experimental and clinical results with the *Corynebacterium granulosum*-derived immunomodulator P40, Asian Pacific J. Allergy ANG immunol., 984, 2, 144-155), effects on phagocytosis (L. Jacques, B. Bizzini and D. Mathieu, Variation des activités complémentaires et phagocytaires chez les rats brulés. Effet d'une immunostimulation par *Corynebacterium granulosum*, Med. Mal. Infect. 1978, 8, 515-518 and P. Mastroeni, B. Bizzini, L. Bonina, D. Iannello, et al. The restoration of impaired macrophage functions using an immunomodulator the *Corynebacterium granulosum*-deride P40 fraction, Immunopharmacology, 1985, 10, 27-34);

effects on bacterial infections (B. Bizzini and M. Fattal-German. Potentiation by nonspecific immunostimulation of the efficacy of antibiotics in the treatment of experimental bacterial infections, Biomed. Pharmacother., 1989, 43, 753-762), effects on viral infections (M. Fattal-German and B. Bizzini, The *Corynebacte-*

*rium granulosum*-derived P40 immunomodulator exerts a synergistic effect on the activity of antiviral drugs in the treatment of experimental viral infections, Biomed. Pharmacother., 1988, 42, 217-220), cytokine induction (B. Bizzini, M. Carlotti, M. Fattal-German, Induction of various cytokines in mice and activation of the complement system in rats as a part of the mechanism of action of the *Corynebacterium granulosum*-derived P40 immunomodulator, FEMS Microbiol. Immunol., 1992, 105, 171-180), effects on *E. coli* infections (Mathieu, D., Jacques, L., Auer, J. and B. Bizzini, *E. Coli* infections of the lower urinary tract and their treatment by immunomodulation or combined immunomodulation and antigenic therapy, Biomed. Pharmacother., 1988, 42, 271-278).

Many clinical trials have been conducted on P40 fraction in relation to recurrent respiratory system infections (M. R. Ickovic, E. Henocq, E. H. Relyveld and B. Bizzini, Effect of immunomodulation with the *Corynebacterium granulosum*-derived Immunomodulator P40 on patients with recurring respiratory infections. J. Asthma, 1984, 21, 29-33, and E. Henocq, R. Veronesi, E. H. Relyveld and B. Bizzini, Treatment of relapsing chronic infection of the respiratory tract. A comparative study of the effectiveness of non specific immunotherapy with the immunoadjuvant P40 and vaccinotherapy, Rev. Inst. Med. Trop. Sao Paulo, 1984, 26, 105-109), to recurrent genital-urinary tract infections (E. Henocq, G. Arvis, M. C. Delsaux and B. Bizzini, Traitement des infections urogénitales récidivantes par immunomodulation, Ann. Urol., 1985, 19, 371-375), to allergic disorders (E. Henocq, A. Prouvost-Danon and B. Bizzini, Preliminary experimental and clinical results with inactivated allergens conjugated to the *Corynebacterium granulosum*-derived immunomodulator P40, Boll. 1st. Sieroter. Milan., 1987, 66, 70-77) and to breast cancer (J. Reynier, B. Bizzini, J. C Bazin and R. Villet, Immunocompetence, immunostimulation: Experimental facts and clinical perspectives. Advances in Immunomodulation, Eds. B. Bizzini and E. Bonmassar. Pythagora Press: Rome-Milan, 1988, p. 345-362. and Reynier, J. Villet, R. Bazin, J. C. Bizzini, B. Gandrielle, C. et al. Immunological investigation and immunotherapy in patients operated on for breast carcinoma. Int. Surgery, 1982, 67, 17-24).

In the conjugate of the invention, the physiologically acceptable carrier comprises at least one mucopolysaccharide or a mucopolysaccharidic fraction.

Typically, the mucopolysaccharides or sulfated glycosaminoglycans, also known as GAGs, in the conjugate of the invention comprise unbranched polysaccharide chains consisting of repeated disaccharide units. Typically, the repeating units are based on a hexose or an hexuronic acid bound to a hexosamine.

Being hydrophilic, the mucopolysaccharides of the conjugate of the invention may easily bind with water and penetrate into the deepest layers of the skin.

The mucopolysaccharides carry the fraction of bacterial wall and perform an active part in cell functionality, firstly in adhesion, because they are associated to the basal membrane tissues, which are in contact with cells.

Consequently, the conjugate of the fragment of bacterial wall, in particular of P40, and of the mucopolysaccharidic carrier performs the function of facilitating and extending the contact of the fragment of bacterial wall with the skin and to allow the fragment of bacterial wall to fully perform its stimulation effects on the Langerhans cells and on the keratinocytes.

In accordance with some embodiments, the mucopolysaccharides or mucopolysaccharidic fractions contained in the conjugate of the invention are selected from the group comprising hyaluronic acid (HA), chondroitin-4-sulfate (C4SA), chondroitin-6-sulfate (C6SC), dermatan sulfate (DS-condroitin-solfate B), heparin sulfate (HS), heparin (HP) and keratan-sulfate (KS).

Those most present in the human derma are I-HA and DS, whereas lesser quantities of C6SC are found and C4SA HS and HP are mostly present in blood vessels and nerve tissue (R. Fleischmajer et al., Dermal specificity, J. Invest. Dermatol., 1970, 54, 472, K. Meyer et al., The acid mucopolysaccharides of connective tissue, Biochim. Biophys. Acta, 1956, 21, 506).

A suitable mucopolysaccharide is hyaluronic acid, a substance present in skin in single form and as proteoglycan. Typically, the molecular weight may vary according to the tissue from which it is extracted, and is comprised between $7.7 \times 10$ to the fourth power and $6 \times 10$ to the sixth power (T. C. Laurent et al., Fractionation of hyaluronic acid. The polydispersity of hyaluronic acid from the bovine vitreous body, Biochim. Biophys Acta, 1960, 42, 476). It is common in organs and tissues, in particular in synovial fluid (Scher, I., et al. Biochem. J. 1972, 126, 1073), the vitreous body of the eye and connective tissue (H. Schubert et al., A primer on connective tissue biochemistry, 968, Lea and Febiger, Philadelphia). The functions described for this polysaccharide include the capacity of interfering with the intra/extracellular movement of water (J. H. Fessler, A structural function of mucopolysaccharides in connective tissue. Biochem. J., 1960, 76, 124) and of solution (T. C. Laurent et al. Interaction between polysaccharides and the macromolecules. The transport of glomerulal particles through hyaluronic acid solutions, Biochim. Biophys. Acta, & C., 78, 351) and the capacity of stimulating physiological repair and tissue remodeling (B. P. Toole et al., Morphogenic recognition, Ed. S. H. Barondes, 1976, 275, Plenum Press, NY).

Another suitable mucopolysaccharide is chondroitin sulfate. This substance is included in a group of polysaccharides heterogeneous both in terms of structure and sulfation, because it may be sulfated or contain a sulfate in position 4 of the galactosamine (CSA) or in position 6 (CSC), or both positions.

By way of example, the molecular weight of CSA and CSC may be comprised between 5000 and 50,000 (W. D. Comper et al., Physiological function of connective tissue polysaccharides, Physiol. Rev., 1978, 58, 255). Chondroitin sulfate has a high polyanionic load, and this explains its interaction with intracellular migration of compounds according to the bio-mechanisms involved on said level. It is particularly present in cartilage (R. Amado et al., FEBS Lett., 1974, 39, 49).

Another suitable mucopolysaccharide is keratan sulfate. There are two main types of keratan sulfate (KS) (K. Meyer et al., Biochim. Biophys. Acta, 1956, 21, 506), one located exclusively in the cornea and the other present in many skeletal tissues (nucleus pulposus, cartilage, bone).

The greatest difference between the two types is in the protein linkage; indeed, while corneal keratan (KS I) is bound to protein by means of two types of bonds, skeletal keratan (KS II) contains three types of bonds (J. R. Baker et al., Connect. Tissue, 1975, 3, 149).

N-acetylgalactosamine is the component commonly found in repeating disaccharide units of keratan sulfate.

Another mucopolysaccharide which may be present in the conjugate of the invention is dermatan sulfate. This substance was isolated for the first time in pig skin (K. Meyer et al., J. Biol. Chem., 1941, 138, 491). Dermatan sulfate was at first named condroitin sulfate B because the polysaccharides are similar to those of cartilage condroitin sulfate (K. Meyer et al., Biochim. Biophys. Acta, 1956, 21, 506).

Later, it was also called beta-heparin having been also isolated in lung extracts used for the production of heparin (R. Marbet et al., Helv. Chim. Acta, 1951, 34, 2311).

Dermatan sulfate was later isolated in many other tissues, such as gastric mucosa (H. Smith et al., Biochem. J., 1953, 53, 666), heart valves (Meyer, 1956) and umbilical cord (I. Danishefsky et al., J. Biol. Chem., 1966, 241, 143).

The pharmacological properties of dermatan sulfate include anti-clotting (I. Volpato et al., Substantially pure dermatan sulfate and heparan sulfate glycosaminoglycans and their pharmaceutical use, EP 97625/2004) and the capacity of regenerating nerve tissue sampled using the pheochromocytoma induction test in rats after NGF (nerve growth factor) destruction (B. Bizzini and I. Volpato, unpublished research).

Heparan sulfate is also a suitable carrier of the conjugate of the invention. It typically has a low degree of sulfation and iodination (S. I. Lamberg et al., Glycosaminoglycans. A biochemical and clinical review, J. Invest. Dermatol., 1974, 63, 433).

Heparan sulfate essentially differs from heparin in that it is an ubiquitous component on the cellular surface of many types of cells and it is present in form of proteoglycan, whereas heparin is stocked in mastocyte granules from where it can be released in response to given stimuli and where it performs important intracellular functions (P. M. Kraemer, Biochemistry, 1971, 1437).

It has been seen that the cellular production of this polysaccharide on dermal level increases with ageing contrary to that of hyaluronic acid, which decreases instead (G. Sluke et al., Humandiploid fibroblast, Mech. Ageing Dev., 1981, 16, 19).

The glycosaminoglycans sulfate of the HS, DS, C6S-C, C4S-A ks Eha type are capable of influencing cellular function mechanisms, such as adhesion (H. K. Kleinman et al., Cell Biol., 1981, 88, 473), migration (B. P. Toole in Cell Biology of Extracellular Matrix. E. D. Hay, Ed., 1981, 275, Plenum Press NY), proliferation (C. Grobstein et al., In extracellular matrix influences gene expression, H. G. Slavkin and R. C. Grenlich, Eds., 1975, p. 9-16 and 804-814 Academic Press, NY) and differentiation (A. Vaheri et al., in Cellular Control in Differentiation, C. W. Loyd and D. A. Rees, Eds, 1981, 29, Academic Press, NY) and are directly associated to the cellular surface (P M; Kraemer, Biochemistry, 1971, 10, 1437) or to the basal membrane tissues which are in contact with the cells (Y. S. Kanwar et al., Proc; Natl. Acad. Sci. USA, 1979, 76, 1303).

In accordance with some embodiments, the conjugate of the invention contains an amount of fragment of wall of Corynebacterium, in particular of Corynebacterium granulosum, comprised from 10 to 200 µg per gram of mucopolysaccharide or fraction thereof.

In accordance with some embodiments, the conjugate of the mucopolysaccharide with the bacterial wall based carrier, in particular fragments of wall of Corynebacterium granulosum (P40), comprises an oxidation reaction of the hydroxyl groups (—OH) present in the mucopolysaccharides to form aldehydes (—CHO) which bind with the amine groups (—NH2) of the peptidic chains present on the surface of the fragments of bacterial wall of Corynebacterium (P40).

The oxidation reaction of the OH groups of the mucopolysaccharides may be obtained using a suitable bland oxidant used in biological techniques, such as for example sodium monoiodoacetate.

In accordance with some embodiments, the mucopolysaccharide oxidation reaction comprises adding the mucopolysaccharide to an aqueous buffer solution with slightly acid pH, e.g. comprised between pH 5 and 6, preferably close to 5.5, to obtain the solution containing the mucopolysaccharide to which an oxidizing agent having a bland oxidizing action is added, such as sodium monoiodoacetate, to oxidize the hydroxyl groups, and optionally block the oxidation reaction, typically by adding a substance containing OH groups, e.g. a glycol, e.g. glycerol.

It is then possible to add fragments of the cellular wall of a bacterium, such as P40, to obtain the conjugate with the oxidized or partially oxidized mucopolysaccharides to the resulting solution.

Suitable techniques may be used for forming bonds between the amino groups present in the bacterial wall fragments, in particular P40 and the —OH groups of the mucopolysaccharides in order to obtain the conjugate of the fragments of bacterial wall and the mucopolysaccharides.

In accordance with an aspect of the invention, the composition of the invention is applied to medicine, in particular dermatology.

The conjugates of mucopolysaccharides and cellular fragments with immunomodulating action of the invention are suitable for topical-mucosal application. Without being absorbed on systematic level, these conjugates have synergistic effects capable of: preventing and curing, for example, allergic and dysfunctional skin manifestations (fat, wrinkles, skin ageing etc.) (HA-P40, C6S-P4O, KS-P40), curing infective, inflammatory and immunity skin disorders, (eczemas, psoriasis, acne, erythemas, burns, diabetic ulcers etc.) (DS-P40, HS-P40 etc.), preventing and curing vascular diseases (varicose veins, phlebitis, thrombophlebitis, peripheral vascular thrombosis etc.) (HS-P40, FMHP-P40 etc.). The action synergism derives from the fact that the mucopolysaccharides in conjugate form applied to the site of the lesion work as carriers of the insoluble particle cellular fragments with immunomodulating action allowing the close contact with the skin tissue in addition to performing their normal therapeutic functions.

This contact is sufficient to promote the activation of the subcutaneous-submucosal immunocompetent cells with consequent promotion of non-specific endogenous immune defense mechanisms.

In accordance with another aspect, the present invention relates to a pharmaceutical composition comprising a conjugate of a fragment of cellular wall of a bacterium belonging to the genus Corynebacterium, in particular P40, and a physiologically acceptable carrier comprising a mucopolysaccharide or a mucopolysaccharidic fraction and a pharmaceutically or physiologically acceptable excipient.

The pharmaceutical composition according to this aspect of the present invention is particularly suited for topical application, and consequently may be any form suitable for topical application.

Typically, the pharmaceutical composition of the invention may be in solid, liquid or semi-solid form.

The solid form comprises formulations in cream, paste, powder, ointment, liniment. The liquid form comprises formulations in form of solution, suspension, oil dispersion in water or water in oil.

The semi-solid form comprises fluids, gels, dermatological serums.

One or more excipients may be present in the composition of the invention used in the formulation techniques of the preparations for topical use, such as for example dispersant agents, anti-clotting agents, surfactants, detergents, suspending agents, mass forming agents, UV ray protection agents etc.

In accordance with some embodiments, the composition of the invention may contain other biologically active substances, such as, for example, plant extracts, vitamins, mineral salts, amino acids, such as arginine.

In accordance with some embodiments, the composition of the invention may comprise one or more pharmaceutically active substances, such as, for example, antibiotics, antivirals, antifungals, FAN or steroidal anti-inflammatory drugs, hormones etc.

In accordance with another aspect, the present invention relates to a conjugate of a fragment of a cellular wall of a bacterium belonging to the genus *Corynebacterium*, in particular P40, and a physiologically acceptable carrier comprising a mucopolysaccharide or a mucopolysaccharidic fraction for use in the treatment of infections, in particular dermatological infections of bacterial, viral or fungal origin.

In accordance with a fourth aspect, the present invention relates to a conjugate of a fragment of a cellular wall of a bacterium belonging to the genus *Corynebacterium*, in particular P40, and a physiologically acceptable carrier comprising a mucopolysaccharide or a mucopolysaccharidic fraction for use in the treatment of dermatological affections or pathologies.

By way of example, the composition of the invention is advantageously applied to the treatment of vaginal mucosae affections, such as fungal, viral or bacterial infections.

In accordance with a fifth aspect, the present invention relates to a conjugate of a fragment of a cellular wall of a bacterium belonging to the genus *Corynebacterium*, in particular P40, and a physiologically acceptable carrier comprising a mucopolysaccharide or a mucopolysaccharidic fraction for topical use in the treatment of skin or mucosae allergy disorders or affections.

By way of example, the composition of the invention is advantageously applied to the treatment of rashes, eczema, itches or erythemas.

In accordance with some embodiments, the composition of the invention is advantageously applied to delay the skin ageing processes.

The present invention claims priority over Italian patent MI2012A001597 filed on 25 Sep. 2012, the content of which is incorporated herein by reference.

The present invention will now be described with reference to the following examples which are supplied by way of illustration only without limiting the invention in any manner.

Example 1

Obtaining of the Particle Fraction of Cellular Wall of *Corynebacterium granulosum* (P40)

It is obtained in accordance with the method described by B. Bizzini et al. (Med. Mal. Inf., 1978, 8, 408) by culture of *C. granulosum* on nutrient broth enriched with glucose in anaerobic conditions at 37° C. for 36 hours. The bacteria are killed by heating the culture for 30 minutes at 60° C. and the mass of microorganisms is then collected by centrifugation at 5000×g for 30 minutes. The bacteria are re-suspended in water and sedimented again. The bacteria are then washed again for second time. The washed microbiotic mass is dried in oven at 50° C. The bacteria are then delipidated by extraction in a Soxhlet subsequently for an 8 hour cycle with: 1) a 1:1 mixture of ethanol and ether; 2) chloroform; 3) a 2:1 mixture of methanol and chloroform. The delipidated bacteria are returned into a water suspension and crushed in a Waring Blendor. The bacteria which are not broken are eliminated by centrifugation at 1000×g for 5 minutes. A fraction is precipitated by adding an ammonium sulfate solution to 40% saturation from the surnatant containing the fragmented bacteria. The precipitate is left to decanter overnight at 4° C. and collected by centrifugation at 10,000×g for 15 minutes. The sediment is re-hydrated and dialyzed versus water to eliminate all traces of ammonium sulfate. It is lyophilized.

Yield: 10-20%.

The reticulo-stimulating activity of the P40 fraction is determined by means of the splenomegaly test in recipient mice by intravenous administration 50 μg of P40. The mice were sacrificed 7-8 days after the injection and the weight of their spleen was compared with that of a group of control mice which had received physiological saline. The K (simulated animals)/K0 (control animals) activity index must be higher than 2.

Example 2

Conjugate of Hyaluronic Acid and P40 Fraction

Obtaining of HA-P40

5 g of sodium hyaluronate are dissolved in 100 ml of acetate buffer 0.05 M, pH 5.5 with agitation to obtain a solution which is not excessively viscose. 856 mg of sodium monoiodoacetate are then added to the solution and oxidation reaction is allowed at ambient temperature away from light for 30 minutes. The reaction is then blocked by adding 1 ml of glycerol 5 M. After 15 minutes of reaction, the pH is adjusted to about 9 by adding sodium carbonate in powder form, after which 5 g of P40 are added to the solution (100 stimulating units) and conjugation is left to occur at ambient temperature for several hours with agitation and overnight at 4° C. without agitation. The aldehydic groups which are still free may be blocked by adding 5 ml of a solution of 1M of an amino acid, such as arginine. The conjugate solution is dialyzed in water and lyophilized after 30 minutes.

Example 3

Conjugate of Dermatan Sulfate and P40 (DS-P40)

5 g of Dermatan sulfate are dissolved in 40 ml of acetate buffer 0.05 M pH 5.5. 856 mg of sodium monoiodoacetate are added to the solution and allowed to react away from light with agitation at ambient temperature for 30 minutes, after which the excess of MIA is deactivated by adding 1 ml of glycerol 5 M. The pH of the oxidized Dermatan sulfate solution is adjusted to about 9 and 5 mg of P40 are added (100 stimulating units) and conjugation is allowed for a few hours at ambient temperature and overnight at 4° C. without agitation. The aldehydic groups which do not react may be blocked by adding 1 ml of a solution of an amino acid, such as arginine. The conjugate solution is dialyzed with water and lyophilized after half an hour.

Example 4

Conjugate of Heparan Sulfate and P40 (HS-P40)

5 g of Heparan sulfate are dissolved in 30 ml of acetate buffer 0.05 M pH 5.5. 428 mg of sodium monoiodoacetate (MIA) are added to the solution and allowed to react away from light with agitation at ambient temperature for 30 minutes, after which the reaction is blocked by adding 0.5 of glycerol 5 M. Sodium carbonate in powder is added to adjust pH to about 9 after 30 minutes. 5 mg of P40 is added and the conjugation is left to occur with agitation at ambient temperature for 1 M, preferably such as arginine, overnight at 4° C., without agitation. The aldehydic groups which are still free are blocked by adding 2.5 ml of a solution of an amino acid 1 M and after 30 minutes the conjugate solution is dialyzed versus water and lyophilized.

Example 5

Conjugate of (Fast Moving) Heparin and P40 (FMHP-P40)

5 g of low molecular weight fast moving heparin (<5 KDa) are dissolved in 30 ml of acetate buffer 0.05 M, pH 5.5 and 428 mg of sodium monoiodoacetate (MIA) are added to this solution away from light with agitation and reaction is allowed for 30 minutes at ambient temperature for 30 minutes after which the reaction is blocked by adding 0.5 ml of glycerol 5 M. The pH of the solution is adjusted to about 9 by adding sodium carbonate in powder. 5 mg (100 simulating units) of P40 are then added. After 24 hours at the end of the reaction at laboratory temperature, 2.5 ml solution are added of a solution of amino acid 1 M, such as arginine, for blocking the aldehydic groups which are still free. The conjugate solution is dialyzed versus water and lyophilized after 30 minutes.

Example 6

Conjugate of Chondroitin-6-Sulfate AC and P40 Fraction (C-6SC-P40) or (C4SA-P40)

5 g of C6SC or C4SA are dissolved in 30 of buffer acetate 0.05 M, pH 5.5, 856 mg of sodium monoiodoacetate (MIA) are added to this solution and reaction is allowed for 30 minutes at ambient temperature away from light with agitation. The reaction is then blocked by adding 1 ml of glycerol 5 M. The pH of the solution is adjusted to about 9 by adding sodium carbonate in powder. 5 mg of P40 fraction (100 stimulating units) are then added to this solution and the reaction is allowed away from light with agitation for a few hours at laboratory temperature and then overnight at 4° C. without agitation. The aldehydic groups which are still free are blocked by adding 1 ml of a solution of an amino acid 5 M, such as arginine, after which conjugate solution is dialyzed versus water and lyophilized.

Example 7

Testing of the Composition of the Conjugates of Mucopolysaccharides and the Cellular Wall Particle Fraction of *C. granulosum* P40

The composition of GAGs and P40 conjugates is established by ELISA after marking the conjugates with biotin. The ELISA to be developed comprises the following steps:
1) plate sensitization with AVIDIN;
2) fixing of the conjugate to be tested by marking it with biotin;
3) detecting of the P40 fraction by means of anti-P40 antibodies marked with an enzyme, on one hand, and detecting of the GAG used as carrier by means of the corresponding antibody marked with an enzyme, on the other.

7.1 Testing of the Preventive and Curative Activity of the GAG-P40 Conjugates

The therapeutic stimulation activity of the conjugates is determined by measuring the effect of applications of the preparation containing the conjugate to be tested by intranasal administration versus a *S. pyogenes* A (strain 56-1) infection caused by intranasal administration in the standardized conditions established by B. Bizzini and M. Fattal-German (Standardized infection models as a way of evaluating the potency of anti-infectious agents, Develop. Biol. Standard. 1992, 77, 137-142, Karger, Basel).

7.2 GAGs Characterization Using Anti-GAGs Polyclonal Antibodies

The GAGs structure and the possible structural alterations as a consequence of P40 conjugation are characterized by evaluating the degree of reactivity of the various polysaccharides versus the specific polyclonal antibody.

The various GAGs antibodies were produced in rabbits using GAG-KLH (Keyhole Limpet Hemocyanin) derived as immunogen.

The animals were sensitized for 0 time for subcutaneous administration of the immunogen (1 mg) in 20 points on the shaved skin of the back by volume of 0.05 ml each in complete Freund's adjuvant. 0.5 mg recalls were administered intramuscularly every month in Freund's adjuvant. The production of antibodies was followed by double diffusion in gel of increasing dilutions of serum. Having reached a rather high titration, the serums were taken by cardiac puncture and the IgG fraction was precipitated at 40% of saturation with ammonium sulfate. The marking of the purified antibodies with enzyme were carried out by reaction with glutaraldehyde.

The conjugate/corresponding GAGs reactivity ratios are shown in the following table:

| Conjugate | GAG | Conjugate/GAG ratio |
|---|---|---|
| HA-P40 | HA | 0.95 |
| DS-P40 | DS | 0.87 |
| HS-P40 | HS | 0.91 |
| HPFM6P40 | HPFM | 0.77 |
| C6SC-P40 | C6SC | 0.82 |
| C4SA_P40 | C4SA | 0.76 |

Example 8

Analysis of Efficacy on UV Erythema in Rats

Wistar rats weighing approximately 200 g were appropriately shaved in the dorsal area. Under ether anesthesia they were exposed to UV rays for 2 hours sufficient to induce an evident skin erythema.

The animals were subsequently treated in the erythema affected area using a ointment based on the various conjugates in concentration corresponding to that of P40 for therapeutic use (50 μg per application).

The application was repeated daily (one a day) to total remission of the edema. The experiment was conducted by comparing with animals to which a placebo ointment was applied (controls) and animals to which a liniment based on single mucopolysaccharides (not conjugated) was applied.

The reduction of the area of the erythema was evaluated during the 7 days following the application of the various conjugates.

The table below shows the percentage reduction over time, 100 being the extension of the UV induced erythema (zero time).

Percentage reduction of UV induced erythema UV on the back of rats

| Group | Treatment | \multicolumn{7}{c}{Percentage reduction of erythema after number of days} | | | | | | |
|---|---|---|---|---|---|---|---|---|
| | | 1 | 2 | 3 | 4 | 5 | 6 | 7 |
| 1 | Placebo (control) | zero | zero | zero | 5.0 | 10.0 | 10.0 | 18.0 |
| 2 | P40 | 30.0 | 38.0 | 50.0 | 70.0 | 100.0 | | |
| 3 | HA | 10.0 | 20.0 | 25.0 | 30.0 | 40.0 | 50.0 | 70.0 |
| 4 | DS | 35.0 | 45.0 | 60.0 | 75.0 | 90.0 | 100.0 | |
| 5 | HS | 35.0 | 40.0 | 60.0 | 70.0 | 85.0 | 100.0 | |
| 6 | HPFM | 20.0 | 45.0 | 55.0 | 60.0 | 80.0 | 100.0 | |
| 7 | C6SC | 15.0 | 20.0 | 35.0 | 45.0 | 60.0 | 70.0 | 85.0 |
| 8 | HA-P40 | 30.0 | 50.0 | 80.0 | 100.0 | | | |
| 9 | DS-P40 | 50.0 | 85.0 | 100.0 | | | | |
| 10 | HS_P40 | 50.0 | 65.0 | 100.0 | | | | |
| 11 | HPFM-P40 | 45.0 | 70.0 | 80.0 | 100.0 | | | |
| 12 | C6SC-P40 | 60.0 | 65.0 | 80.0 | 100.0 | | | |

At different levels of efficacy, the various mucopolysaccharides (HA, DS, HA, C6SC, HPFM) are capable of accelerating erythema resolution by virtue of their anti-inflammatory pharmaceutical effects, blood micro-circulation effects, and effects on basal membrane activation and cellular reproduction.

This effect is significantly increased by the conjugation with the non-specific immunomodulating particle fraction of P40.

The synergism is due to the activation of the bio-mechanisms at the base of the functionality and cellular exchange consequent to the macrophage stimulation and the completion system due to the aforesaid fraction.

Example 9

Analysis of the Efficacy of Infection Induced in Mice by Intranasal Inoculation of S. pyogenes The method described by B. Bizzini et al. (FEMS Microbiol. Immunol. 1990, 64, 155) was used.

The products were applied with dose corresponding to 100 µg of P40/kg by body weight into the nostrils of the mice for 3 days before and on the same day as the S. pyogenes infection (2×10 to the sixth power of bacteria) intranasal inoculation. Ten batches of mice were used and compared with a group not treated with P40 (control) and various GAGs and the respective conjugates with P40.

The survival percentage during the 7 days following the treatment was monitored.

Survival percentage following intranasal infection of S. pyogenes

| Group | Treatment | Dose µg or mg/kg | \multicolumn{4}{c}{Survival percentage after number of days} | | | |
|---|---|---|---|---|---|---|
| | | | $1^{st}$ | $3^{rd}$ | $5^{th}$ | $7^{th}$ |
| 1 | controls | — | 90 | 20 | zero | |
| 2 | P40 | 100 µg | 100 | 100 | 100 | 80 |
| 3 | HA | 75 mg | 100 | 40 | zero | |
| 4 | DS | 50 mg | 100 | 50 | zero | |
| 5 | HS | 50 mg | 100 | 50 | zero | |
| 6 | C6SC | 75 mg | 90 | 40 | zero | |
| 7 | HPFM | 50 mg | 90 | 30 | zero | |
| 8 | HA-P40 | (100 µg P40) | 100 | 90 | 90 | |
| 9 | DS-P40 | (100 µg P40) | 100 | 100 | 100 | |
| 10 | HS-P40 | (100 µg P40) | 100 | 100 | 100 | |
| 11 | HPFM-P40 | (100 µg P40) | 100 | 100 | 100 | |
| 12 | C6SC-P40 | (100 µg P40) | 100 | 100 | 90 | |

The P40 property of inhibiting the onset of the infections is not altered by the conjugation with GAGs.

The latter do not show any interaction with the S. pyogenes infection.

Example 10

Analysis of the Efficacy on HSV Infection Induced in Mucosa in Rats

A HSV-1 moderated type vaginal infection was induced in rats following the method of M. Fattal-German and B. Bizzini (Develop. Biol. Standard., 1992, 77, 115).

The animals were split into groups of 10 units each.

We waited for 3 days for the symptoms of the infection to appear in all animals. At this point, the treatment was started by daily applying of a gel containing the various studied compounds in a concentration corresponding to 50 µg of P40/application/day on mucosa level.

The total symptom remission time of the treated, control and reference animals was monitored.

Remission time/number of animals in HSV-1 infective symptoms on mucosa level

| Group | Treatment | Dose µg or mg/kg | \multicolumn{5}{c}{Number of rat with remission of symptoms after number of days} | | | | |
|---|---|---|---|---|---|---|---|
| | | | $1^{st}$ | $3^{rd}$ | $5^{th}$ | $7^{th}$ | $10^{th}$ |
| 1 | Controls | — | 0/10 | 0/10 | 0/10 | 0/10 | 0/10 |
| 2 | P40 | 50 µg | | 1/10 | 3/10 | 8/10 | 10/10 |
| 3 | HA | 25 mg | | 0/10 | 0/10 | 0/10 | 0/10 |
| 4 | DS | 25 mg | | 0/10 | 0/10 | 0/10 | 1/10 |
| 5 | HS | 25 mg | | 0/10 | 0/10 | 1/10 | 2/10 |
| 6 | HPFM | 25 mg | | 0/10 | 0/10 | 0/10 | 1/10 |
| 7 | C6SC | 25 mg | | 0/10 | 0/10 | 0/10 | 0/10 |
| 8 | HA-P40 | 50 µg P40 | | 2/10 | 5/10 | 10/10 | |
| 9 | DS-P40 | 50 µg P40 | | 4/10 | 10/10 | | |
| 10 | HS-P40 | 50 µg P40 | | 8/10 | 10/10 | | |
| 11 | HPFM-P40 | 50 µg P40 | | 5/10 | 10/10 | | |
| 12 | C6SC-P40 | 50 µg P40 | | 4/10 | 8/10 | 10/10 | |

The P40 immunomodulator is capable of resolving the symptoms deriving from the mucosal application of the herpes virus in a few days.

This property is potentiated and accelerated by effect of the conjugation of the immunomodulator and the GAGs capable of allowing excellent contact with the mucosa.

The fact that some P40 conjugates with different GAGs, such as DS-P40, HS-P40 and FMHP-P40, are more active indicates a synergistic influence on cell vitality and reproduction of the non-specific immunomodulating activities of P40 and the mucopolysaccharide properties.

Example 11

Analysis of the Efficacy in Thrombosis Induced by Morrhuate Sodium in the Ear of Rabbits The thrombus was induced in the marginal vein of the previously shaved ear of rabbits isolated by approximately 3 cm using hemostatic clamps and injecting 0.2 ml of a 5% solution of morrhuate sodium in the isolated site.

The hemostatic clamps were removed after 10 minutes once the thrombus was consolidated.

200 mg of gel containing 10 mg of the studied conjugate was applied daily to the concerned area. The remission percentage entity of the thrombus was monitored daily for 10 days.

The table below shows the average reduction percentages over the various days by comparing animals treated with the products of the patent, control animals (not treated) and animals treated with the various conjugation intermediates.

| Group | Treatment | Dose mg/die | Reduction percentage of the experimental thrombus after number of days | | | | |
|---|---|---|---|---|---|---|---|
| | | | $2^{nd}$ | $4^{th}$ | $6^{th}$ | $8^{th}$ | $10^{th}$ |
| 1 | controls | — | | | | | |
| 2 | HA | 25 | — | — | 5 | 15 | 35 |
| 3 | DS | 25 | — | 15 | 25 | 50 | 75 |
| 4 | HS | 25 | 10 | 35 | 70 | 100 | |
| 5 | HPFM | 25 | — | 25 | 60 | 90 | 100 |
| 6 | C6SC | 25 | — | 5 | 15 | 35 | 60 |
| 7 | HA-P40 | 25 | — | 10 | 25 | 35 | 50 |
| 8 | DS-P40 | 25 | — | 25 | 40 | 70 | 100 |
| 9 | HS-P40 | 25 | 25 | 50 | 90 | 100 | |
| 10 | HPFM-P40 | 25 | 10 | 35 | 75 | 100 | |
| 11 | C6SC-P40 | 25 | — | 15 | 35 | 60 | 90 |

P mucopolysaccharides of the HS, FMHP and DS type are capable of resolving the experimental thrombus induced in the animal's vein.

This effect is potentiated by conjugation with P40 (reticulo-stimulating action particle structure).

Potentiation is likely to be due to an acceleration of the distribution of the necrotic cells present in the thrombus due to the stimulation of the macrophage cells.

Example 12

Study of Transdermal Non-Absorption of P40 Conjugates by Topical Application

A specific study was conducted to demonstrate the absence of crossing and prove that the reticulo-stimulating action of the P40 conjugates with the various GAGS is not due to transdermal crossing.

Conjugates prepared with the P40 fraction marked with biotin as tracing molecule were used for this study. The experimental model used is based on the spectrophotometric measurement of biotin by explanting human skin ex vivo (the explantation consisting of dermal and epidermal layers). In this model, biotin was used as control because the explanted skin is impermeable to this molecule.

The in vitro evaluation of the filmogenic action, meaning the capacity of the substances to bind with the surface cutaneous structures without modifying the barrier function and permeability of the same, was carried out at the Vitroscreen laboratory, Via Mose Bianchi 103 20149 Milan, Italy.

No transdermal crossing was found in the study of neither the three conjugates used (HA-P40-biotin, HS-P40-biotin, DS-P40-biotin) nor of the Sulfo-NHS-LS Biotin used as control.

Given the results of the study, it can be concluded that the action of the various P40 conjugates with GAGs occurs without transdermal crossing.

Example 13

Analysis of the Effects on Topical-Mucosae Infections

Individuals were selected affected by:
lip herpes
vaginal candidosis

The various conjugates in pharmaceutical gel form containing 3% of active principle were applied on the infected site once a day.

The treatment was continued for 7 days, average complete remission time of the pathology by the GAGs-P40 conjugates.

The presence of relapse was monitored for the following six-month period. The results are shown in the table below.

| Group | Product | Treatment | Appl./day | Pathology | Remission After number of days | Relapse % After 6 months |
|---|---|---|---|---|---|---|
| $1^{st}$ | P40 | topical gel | one | lip herpes | 2 or 3 | zero |
| $2^{nd}$ | HA | " | " | " | >10 | 70 |
| $3^{rd}$ | DS | " | " | " | " | 50 |
| $4^{th}$ | HS | " | " | " | " | 70 |
| $5^{th}$ | HPFM | " | " | " | " | 90 |
| $6^{th}$ | C6SC | " | " | " | " | 90 |
| $7^{th}$ | HA-P40 | " | " | " | 1 or 2 | zero |
| $8^{th}$ | HS-P40 | " | " | " | 1 or 2 | zero |
| $9^{th}$ | HPFM-P40 | " | " | " | 1 to 3 | 10 |
| $10^{th}$ | C6SC-P40 | " | " | " | 2 or 3 | 20 |
| $1^{st}$ | P40 | " | two | vaginal candidosis | 1 to 4 | 20 |
| $2^{nd}$ | HA | " | " | vaginal candidosis | >10 | 90 |
| $3^{rd}$ | HS | " | " | vaginal candidosis | " | 100 |
| $4^{th}$ | HA-P40 | " | " | vaginal candidosis | 1 or 2 | 10 |
| $5^{th}$ | DS-P40 | " | " | vaginal candidosis | " | 10 |

The result of this experiment was that the particle fraction of P40 performes an immunomodulating activity capable of effectively contrasting lip herpes and vaginal candidosis, whereas the GAGs alone were found to be ineffective. However, the P40 conjugation with GAGs translated into a potentiation of its effect, probably because the contact of the conjugates with the mucosa is closer and more protracted with respect to that of P40 alone.

Example 14

Effect of the GAGs-P40 Conjugates on Acne

Acne is an inflammatory disease with a complex pathogenesis, characterized by the formation of pimples consisting of sebum, keratin and microorganisms.

A group of young volunteers affected by superficial acne were treated with P40 or HA-P40 or DS-P40 or HS-P40 conjugates in non-greasy pharmaceutical gel form, each topical application being equal to 50 μg of P40. The gel was applied once a day in the evening before going to bed for 10 days after carefully washing the face with mild detergent.

All products were found capable of significantly improving acne lesions with the itchiness disappearing a few days after treatment. Most of the comedones had disappeared with the use of the product based on immunomodulating fraction of P40 alone after 10 days of treatment, or sooner with the GAGs-P40 conjugates.

Example 15

Effect of the GAGs-P40 Conjugates on Psoriasis

A volunteer group affected by non-invasive psoriasis were treated by topical application of either P40 or GAGs-P40 conjugates, such as HA-P40 or DS-P40 or HS-P40, in non-greasy pharmaceutical gel form containing 3% of active principle twice a day for 10 days.

A positive response to the treatment, consisting in the disappearance of lesions and itchiness, was observed in most individuals starting from the fifth day of treatment, while a smaller group of individuals did not respond to the treatment. The improvement was particularly apparent when GAGs-P40 conjugates were applied.

Example 16

Effect of the GAGs-P40 Conjugates on Rashes

A rash is the result of an anaphylactic reaction strictly limited to the skin and to the subcutaneous tissues.

Volunteers affected by acute rash were treated with the immunomodulating fraction of P40 or with GAGs-P40 conjugates, such as HA-P40, DS-P40, HS-P40, in pharmaceutical gel form containing 3% of active principle.

Topical applications twice a day for 6 days.

Itchiness considerably decreased or was greatly attenuated after the first applications. Rash lesions prevalently disappeared after 1 or 2 days of treatment, in particular with the application of GAGs-P40 conjugates.

The invention claimed is:

1. A method for modulating a skin and/or mucosa immune or antibody response in a subject, said method comprising:
applying to the skin or mucosa of a subject in need thereof, an effective amount of a composition comprising a conjugate, said conjugate comprising a fragment of a cellular wall of *Corynebacterium granulosum* P40 and a physiologically acceptable carrier, wherein the physiologically acceptable carrier comprises a mucopolysaccharide or a mucopolysaccharidic fraction, wherein said applying modulates the immune response or antibody response in said skin or mucosa.

2. The method of claim 1, wherein the physiologically acceptable mucopolysaccharide or mucopolysaccharidic fraction of the conjugate is selected from hyaluronic acid, chondroitin-4-sulfate, chondroitin-6-sulfate, dermatan sulfate, heparan sulfate, heparin, keratan-sulfate and mixtures thereof.

3. The method of claim 1, wherein the fragment of the cellular wall of *Corynebacterium granulosum* P40 is an insoluble fraction isolated from a delipidated cellular wall of *Corynebacterium granulosum*.

4. The method of claim 1, wherein said conjugate of the composition comprises 10-200 μg of the cellular wall of *Corynebacterium granulosum* P40 per gram of said mucopolysaccharide or mucopolysaccharidic fraction.

5. The method of claim 1 further comprising:
selecting a subject having a dermatological bacterial, viral, or fungal infection, wherein said composition is applied to the skin or mucosa of said subject at the location of said infection.

6. The method of claim 1 further comprising:
selecting a subject having an allergic skin disorder or affection, wherein said composition is applied to the skin of said subject at the location of the allergic skin disorder or affection.

7. The method of claim 6, wherein the allergic skin disorder or affection is a rash, eczema, or erythema.

8. The method of claim 1, wherein the composition is formulated as a cream, paste, powder, ointment, or liniment.

9. The method of claim 1, wherein the composition is formulated as a solution, suspension, or oil dispersion in water.

10. The method of claim 1, wherein the composition is formulated as a fluid, gel, or dermatological serum.

11. The method of claim 1, wherein the composition further comprises one or more excipients selected from the group consisting of a dispersant agent, an anti-clotting agent, a surfactant, a detergent, a suspending agent, a mass forming agent, and a UV ray protection agent.

12. The method of claim 1, wherein the composition further comprises one or more additional biologically active substances selected from the group consisting of a plant extract, vitamins, mineral salts, and amino acids.

13. The method of claim 1, wherein the composition further comprises one or more pharmaceutically active substances selected from the group consisting of an antibiotic, an antiviral, an antifungal, a steroidal anti-inflammatory drug, and a hormone.

14. The method of claim 1, wherein said applying said conjugate to the skin or mucosa of the subject promotes the immune response or antibody response in said skin or mucosa.

* * * * *